(12) United States Patent
Anderson

(10) Patent No.: US 6,810,714 B2
(45) Date of Patent: Nov. 2, 2004

(54) DEVICE FOR REFRIGERANT LEAK SEALANT ADDITIVE DETECTION

(75) Inventor: J. Douglas Anderson, West Chester, PA (US)

(73) Assignee: Neutronics Inc., Exton, PA (US)

(*) Notice: Subject to any disclaimer, the term of this patent is extended or adjusted under 35 U.S.C. 154(b) by 10 days.

(21) Appl. No.: 10/348,265

(22) Filed: Jan. 21, 2003

(65) Prior Publication Data

US 2004/0050146 A1 Mar. 18, 2004

Related U.S. Application Data

(60) Provisional application No. 60/411,193, filed on Sep. 17, 2002.

(51) Int. Cl.[7] .................................................. G01M 3/04
(52) U.S. Cl. ......................................................... 73/40
(58) Field of Search ................................ 73/1.25, 1.26, 73/1.57, 38, 40, 40.5 R, 40.7; 252/72

(56) References Cited

U.S. PATENT DOCUMENTS

| | | | |
|---|---|---|---|
| 3,630,914 A | * 12/1971 | Nankee et al. ................ 252/72 |
| 4,442,015 A | 4/1984 | Packo et al. ................... 252/68 |
| 4,524,159 A | * 6/1985 | Barber ........................... 523/177 |
| 4,729,236 A | * 3/1988 | Samborsky .................... 73/1.25 |
| 4,909,277 A | 3/1990 | Vandiver ..................... 137/493.7 |
| 4,976,134 A | * 12/1990 | Potvin ............................ 73/1.16 |
| 5,315,859 A | * 5/1994 | Schommer ..................... 73/1.25 |
| 5,579,995 A | 12/1996 | Giasson et al. ................ 236/53 |
| 5,603,353 A | 2/1997 | Clark et al. ............ 137/614.01 |
| 5,894,741 A | 4/1999 | Durham et al. ................ 62/525 |
| 5,992,438 A | * 11/1999 | Shaw ............................. 137/14 |
| 6,428,292 B1 | 8/2002 | Wallis et al. ................ 418/55.1 |

* cited by examiner

Primary Examiner—Charles D. Garber
(74) Attorney, Agent, or Firm—Drinker Biddle & Reath LLP

(57) ABSTRACT

A device and method for determining the presence or absence of refrigerant leak sealant within the refrigerant charge of air conditioning systems or stores are described. A sensing unit having a seal-forming surface is wetted and placed in fluid communication with a refrigerant access port of the air conditioning system. A depressor opens the refrigerant port and refrigerant begins to flow through the sensing unit. If any leak sealant is present in the refrigerant charge, a sealant plug begins to form on the seal-forming surface and reduces the flow rate of the refrigerant through the sensing unit, thereby indicating the presence of the sealant. Refrigerant charges that do not contain a leak sealant will flow through the sensing unit at a substantially constant rate, indicating the absence of sealant.

5 Claims, 4 Drawing Sheets

DEVICE FOR REFRIGERANT LEAK SEALANT ADDITIVE DETECTION

CROSS-REFERENCE TO RELATED APPLICATION

The present application claims priority from U.S. Provisional Application No. 60/411,193, filed Sep. 17, 2002, which is incorporated herein by reference in its entirety.

FIELD OF THE INVENTION

The present invention relates to a device and method for identifying the presence or absence of a leak sealant additive in air conditioning system refrigerant charges, preferably but not exclusively for the purpose of identifying potential damage risk to air conditioning service, repair, diagnostic or other equipment.

BACKGROUND OF THE INVENTION

Government regulations in the United States, and in many other countries, require the control of refrigerant releases during air conditioning system service and repair due to the potential damaging effects of fluorocarbon refrigerants to atmospheric ozone levels. Fluorocarbon refrigerants, for example R12, R22, R500 and R502, are suspected of presenting an environmental threat due their potential to deplete the earth's atmospheric ozone layer. Production of these refrigerants has been or is being discontinued by various manufacturers in accordance with the Montreal Protocol. Alternative refrigerants, such as R134a (tetrafluoroethane) for example, are now being utilized that will lessen, but will not totally remove, the potential for atmospheric ozone depletion.

Air conditioning technicians use various service and diagnostic equipment designed to limit the release of all refrigerants to the environment. Such equipment includes, but is not limited to, refrigerant identification analyzers, refrigerant recovery equipment, refrigerant recycling equipment, and refrigerant charging equipment.

Numerous studies of air conditioning servicing and discussions with air conditioning repair technicians indicates that the single largest contributor to refrigerant releases to the atmosphere is air conditioning system leaks. Air conditioning system leaks are also the leading cause of air conditioning system malfunctions in the industry. Air conditioning system leaks contribute to poor air conditioning system performance, increased customer complaints, increased costs to customers due to refrigerant charge replacement, and environmental damage. Costs of refrigerant charge replacement are ever increasing as the cost of original and alternative refrigerants increases.

To lessen the affect of air conditioning system refrigerant leaks upon the customer and the environment, several manufacturers have developed air conditioning system leak sealant additives. These additives come in a variety of formulations from numerous manufacturers. Examples of such leak sealant additives are Super Seal ProTM from Cliplight Manufacturing Company of North York, Ontario, Canada; CRYOsealTM Self-Sealing Kits from Cryo-Chem International of Brunswick, Ga., USA; Keep-It-KoolTM from Mobilair 2000 of Toronto, Ontario, Canada; and R-134a Leak StopTM from Technical Chemical Company of Cleburne, Tex., USA, to name a few. Additionally, virgin refrigerants that contain a leak sealant additive are now available directly from refrigerant manufacturers.

All of these leak sealant additives are designed to seal air conditioning leaks in air conditioning metal components. Specifically, the additives are designed to seal leaks in metal components such as evaporator cores where access is difficult with conventional leak detectors. The additives are typically added to the refrigerant charge as a one or two part liquid and are distributed throughout the air conditioning system via refrigerant circulation by the system compressor. When a leak develops in an air conditioner metal component, the leak sealant additive will be delivered to the leak point by the escaping refrigerant and produce a permanent seal over the leak path, typically in one of two ways. The most common method of seal formation involves the exposure of the sealant to moisture. Moisture is provided by the rapid expansion of refrigerant gas through the leak path, which provides cooling and condensation of atmospheric water vapor at the leak point. Moisture can also be supplied by the condensation that is typically present on all air conditioning system evaporator cores. The additive will then combine with the condensed moisture at the leak to form a permanent seal over the leak path. The other method of seal formation involves the combination of condensed atmospheric water vapor, atmospheric oxygen, and the additive to form a permanent seal over the leak path. Typically, additives that require only exposure to moisture will form a seal on the interior surface of the leak path. Additives that require exposure to moisture and oxygen will typically form a seal within or on the exterior of the leak path. The presence of a leak sealant additive can reduce the environmental impact of refrigerant venting, reduce customer complaints, and limit air conditioning system performance degradation.

However, leak sealant additives can pose difficulties for air conditioning technicians when service is performed upon an air conditioning system that contains a leak sealant additive. The additives will be directly exposed to the diagnostic equipment upon connection to the air conditioning service ports. Since the diagnostic equipment may contain atmospheric water vapor and atmospheric oxygen, the formation of a permanent seal by the additive may be initiated within the equipment itself. Thus, many air conditioning diagnostic tools can be damaged through the clogging of sensing devices, solenoid valves, hoses, gauges, vacuum pumps, etc., by sealant additives. Therefore, air conditioning technicians and manufacturers of air conditioning diagnostic equipment are searching for devices that will either identify the presence of leak sealant additives or provide for their removal to protect expensive diagnostic equipment.

Attempts are currently underway to provide for leak sealant additive removal through filtration. Filtration may involve the removal of refrigerant oil or a liquid—liquid separation filter. Removal of the refrigerant oil from the refrigerant may not serve to totally remove the leak sealant additive since the additives typically are disbursed throughout the refrigerant liquid and vapor phases as well as the refrigerant oil. Liquid-liquid separation may provide an effective method to remove the additives but may require unacceptably high costs to the air conditioning technician. A method of detecting the presence of the leak sealant additive through non-dispersive infrared radiation (NDIR) technology has been developed by the assignee of the present application, Neutronics Incorporated of Exton, Pa., USA. While NDIR technology has provided promising results, it can be expensive.

The present invention utilizes the complete or partial formation of a seal by leak sealant additives and provides a device and method for detecting the presence of sealant additives within an air conditioning system refrigerant charge. The invention is inexpensive, fast, limits refrigerant loss, and easy to use.

SUMMARY OF THE INVENTION

The present invention provides a fast, easy, and inexpensive device and method for detecting the presence of a leak sealant additive within an air conditioning system refrigerant charge or within refrigerant stores. The device is capable of detecting any leak sealant additive in any refrigerant type.

One feature of the present invention is the use of a sensing unit having a passage with a calibrated leak path through which refrigerant can flow. The sensing unit includes a seal-forming surface on which any leak sealant additive can quickly form a seal in the presence of water and/or oxygen to at least partially occlude the passage. The sensing unit is used in combination with a coupler for engaging and opening a refrigerant system service port and a flow indicator for detecting the rate at which refrigerant gas flows through the sensing unit.

In use, the sensing unit can be wetted with ordinary water and connected between the service coupler and flow indicator to form a test rig. The test rig is then connected directly to the air conditioning system or refrigerant storage cylinder service port. Refrigerant from the air conditioning system or storage system will flow through the coupler, sensing unit, and flow indicator. If the refrigerant contains a leak sealant additive, the flow indicator will show a reduction or complete stoppage of refrigerant flow over time as the sealant begins to seal the leak path in the sensing unit. If the refrigerant does not contain a leak sealant additive the flow indicator will indicate a substantially constant refrigerant flow rate over time. Thus, the change in refrigerant flow rate through the sensing unit indicates the presence or absence of a leak sealant additive within the tested refrigerant. If refrigerant flow rate diminishes or ceases totally, then a leak sealant additive is present. Conversely, if refrigerant flow rate remains constant, then no leak sealant additive is present in the refrigerant.

BRIEF DESCRIPTION OF THE FIGURES

Reference is now made to the figures in which.

DETAILED DESCRIPTION OF THE DRAWINGS

Figure 1:
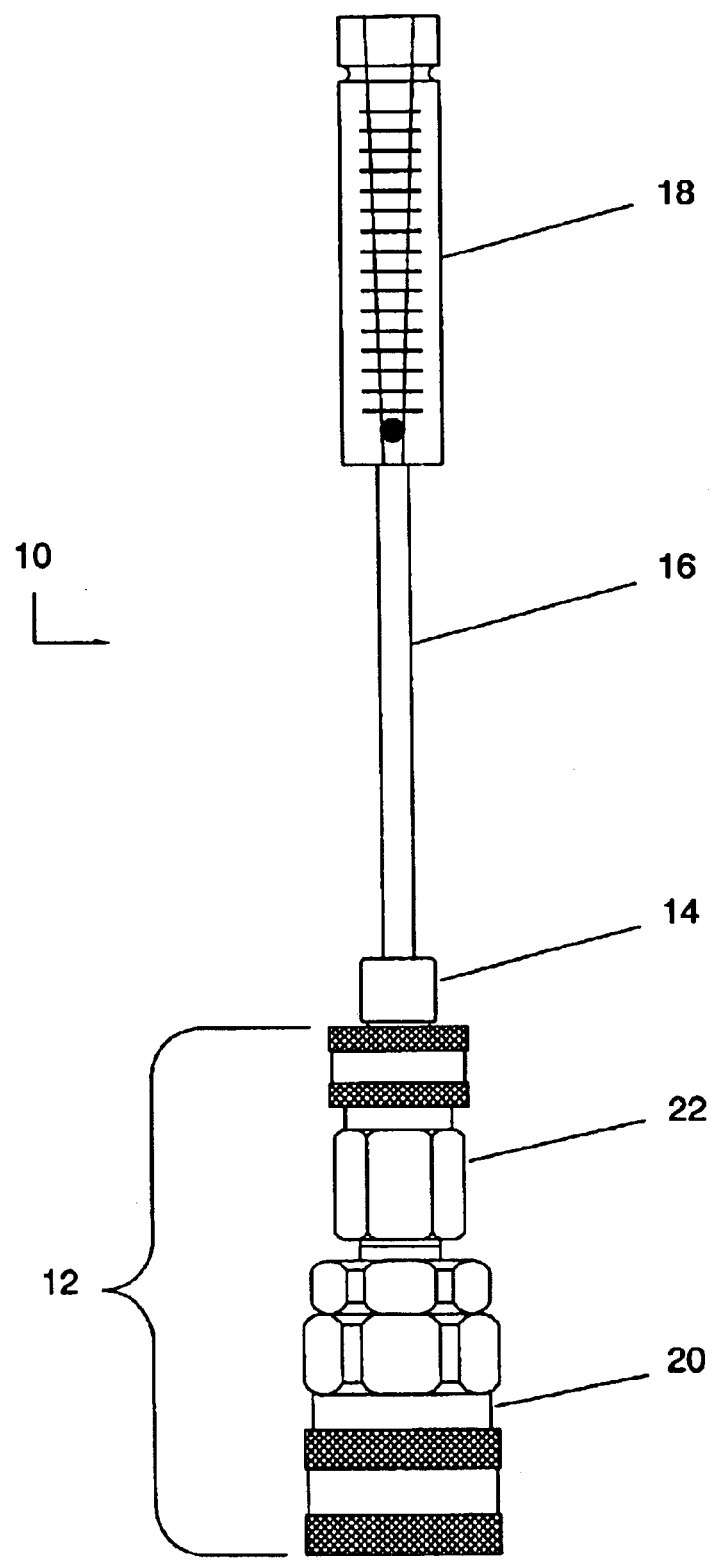
FIG. 1 shows a first embodiment of a test rig according to the present invention, suitable for use with a typical automotive R134a air conditioning system.

In the Figures, in which like numerals indicate like elements, there are shown test rigs and sensing units according to the present invention. FIG. 1 shows a first embodiment of an assembled test rig 10. The test rig 10 is suitable for use with a R134a-based automotive air conditioning system. As is shown by example below, the test rigs of the present invention can be tailored for the specific requirements of other refrigerant-based air conditioning systems through the use of alternative materials, alternative connection components or any other specific requirements of the specific refrigerant-based air conditioning system. The test rigs can be used to detect the presence of a leak sealant additive in virtually any air conditioning system or refrigerant store, including those having halogen-based, fluorocarbon-based, or other non-halogen, non-fluorocarbon based refrigerants and compounds, such as propane, ammonia, carbon dioxide, etc. In use, the test rig 10 is connected to the liquid or high-side port of the air conditioning system or refrigerant store for the extraction of a small portion of the total refrigerant charge.

Figure 3:
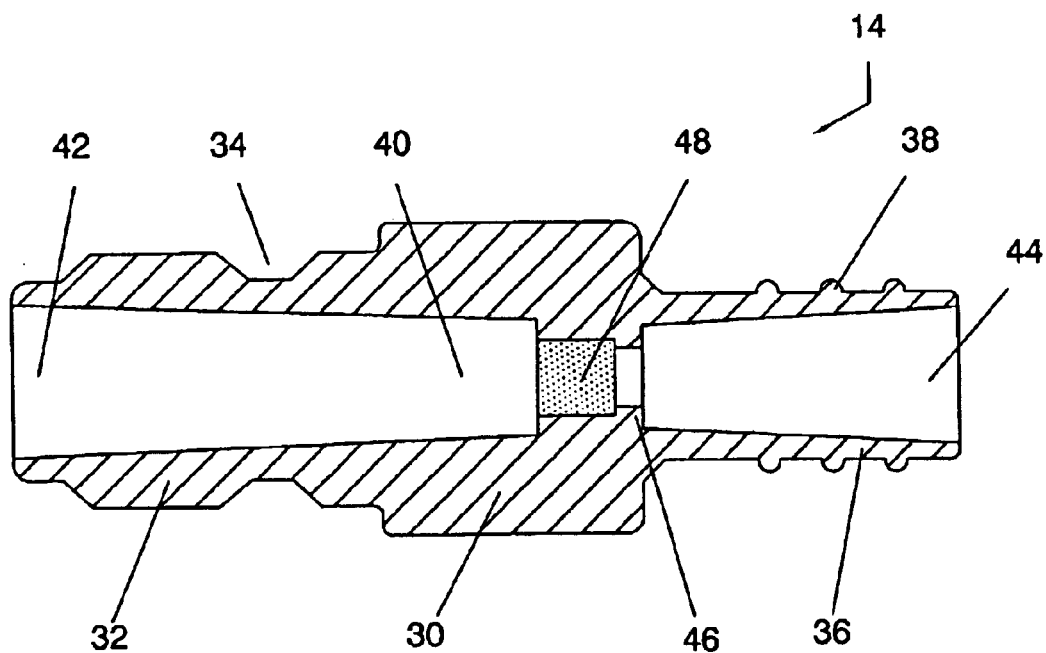
FIG. 3 is a cross-sectional view of a first embodiment of a sensing unit according to the present invention.

Test rig 10 includes a coupler 12, a sensing unit 14, a transfer tube 16 and a flow indicator 18. (The sensing unit 14 is shown in FIG. 3 and described below.) The coupler 12 can be a conventional automotive R134a high-side service coupler 20 and a quick-disconnect fitting 22. The R134a high-side service coupler 20 is sized to connect to the high-side or liquid port of R134a-based air conditioning systems or stores and contains a depressor device that will open such service port valves. The R134a high-side service coupler 20 is a commercially available component known to those skilled in the art. Quick-disconnect fitting 22 is a device that permits easy connection of sensing unit 14 to the coupler 12 and will provide the passage of refrigerant from the coupler 12 to the sensing unit 14. Quick-disconnect fitting 22 is also a commercially available component well known to those skilled in the art. Service coupler 20 and quick-connect fitting 22 can be threaded and screwed together, welded together, or joined by other sealing-type connections.

Transfer tube 16 preferably comprises flexible tubing, suitable for exposure to the specific refrigerant type, that will transfer refrigerant escaping through sensing unit 14 to flow indicator 18. The tube 16 can be formed from flexible neoprene tubing for most refrigerant types. Flow indicator 18 can be a flow meter capable of detecting flow rate in a range suitable for the specific type of air conditioning system. If automotive air conditioning systems are to be tested, the flow indicator 18 should be responsive to flow rates of between about 100 cubic centimeters per minute ($cm^3$/min) to about 1000 $cm^3$/min (about 0.2 to 2 cubic foot per hour). Preferably, the flow indicator 18 is a variable area flow meter having an inlet for connecting to the tube 16 and an indicator ball disposed within a slightly tapered tube. Like the tube 16, the flow indicator is preferably formed using materials capable of withstanding exposure to the specific refrigerant type. However, more economical materials, such as polycarbonate, can also be used.

Figure 2:
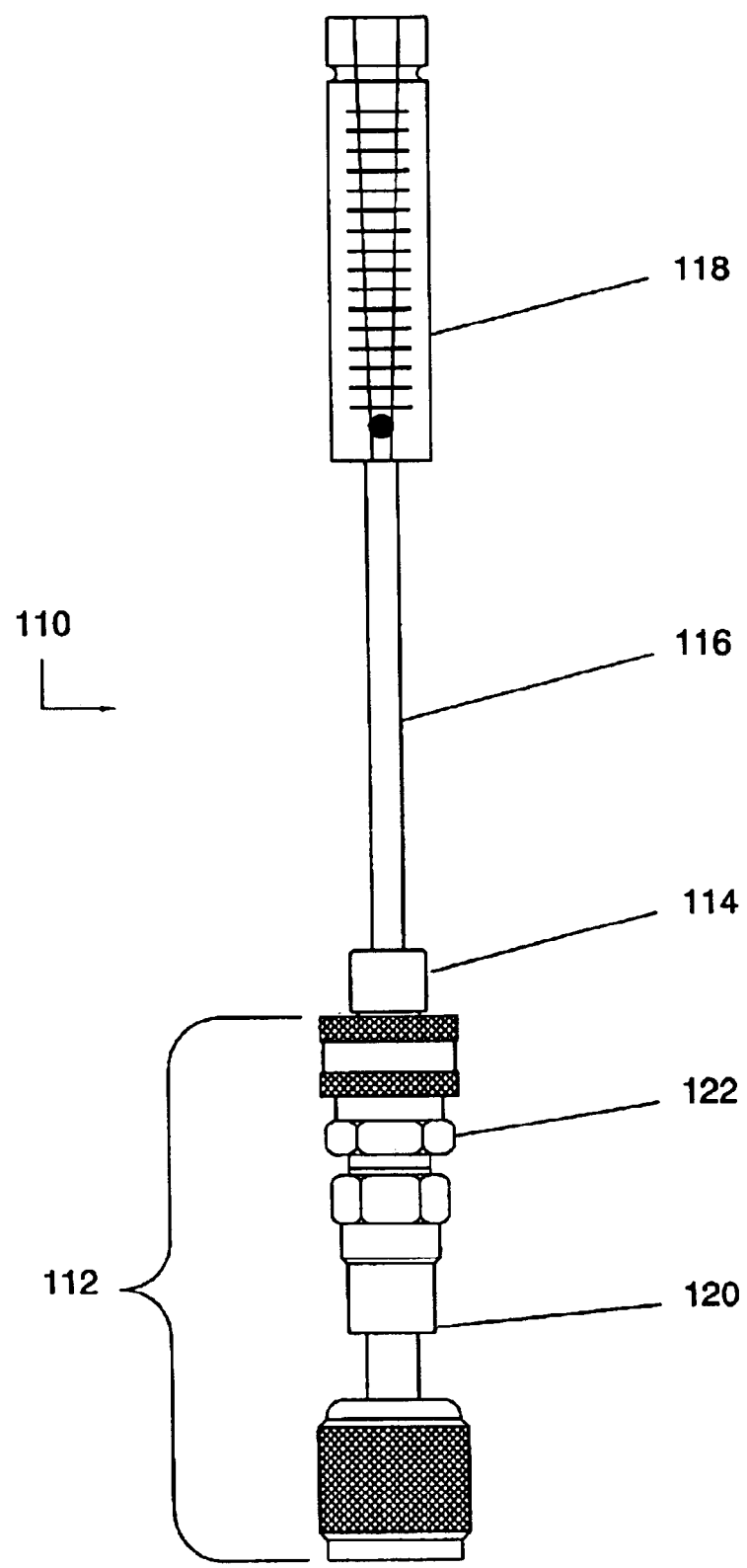
FIG. 2 shows a second embodiment of a test rig according to the present invention, suitable for use with a typical automotive R12 air conditioning system.

A second embodiment of a test rig 110 is shown in FIG. 2. Test rig 110 is adapted for use with an R12-based automotive air conditioning system. Test rig 110 includes a coupler 112, a sensing unit 114, a transfer tube 116 and a flow indicator 118. The coupler 112 can be made using a conventional R12 high-side service coupler 120 and a quick-disconnect fitting 122. The R12 high-side service coupler 120 is sized to connect to the high-side or liquid port of an R12-based air conditioning system or store and contains a depressor device that will open such service port valves. Like the R134a coupler of FIG. 1, such R12 high-side service couplers are commercially available and well known to those skilled in the art. Quick-disconnect fitting 122 is analogous to element 22 of FIG. 1 and similarly permits easy connection of sensing unit 114 to the coupler 112 and provides for the passage of refrigerant from the coupler 112 to the sensing unit 114. Quick-disconnect fitting 122 can be threaded to mate with the R12 high-side service coupler 120. Such quick-disconnect fittings are well known and commercially available. Transfer tube 116 and flow indicator 118 are also similar to their analogous components of the first embodiment.

The sensing unit 14 and sensing unit 114 will now be described with reference to FIGS. 3 and 4. The sensing unit 114 is interchangeable with sensing unit 14. Therefore, sensing unit 14 can be used in place of sensing unit 114 in the test rig 110. Also, sensing unit 114 can be used in place of sensing unit 14 in the embodiment of FIG. 1. Sensing unit 14 and sensing unit 114 are preferably disposable, it being understood that a sensing unit could be reused after a test (more fully described below) if no leak sealant additive is found within the tested system. However, reuse of a sensing unit is not recommended because if used repeatedly the sensing unit could become clogged with oil, dyes, or other materials commonly found around air conditioning systems.

A preferred embodiment of sensing unit 14 is shown in FIG. 3. The sensing unit 14 includes a tubular body 30 that may be made of any suitable material. Brass and molded plastic are two such materials. The tubular body 30 includes an open quick-disconnect end 32 with a recess 34 designed to mate with the quick-disconnect fitting 22 of the test rig 10. Opposite the quick-disconnect end 32 is an open tube stub end 36 with ribs 38 for attaching the transfer tube 16. The tubular body 30 is hollow and defines a passage 40 extending between an inlet 42 at the quick-disconnect end 32 and an outlet 44 at tube stub end 36. The body 30 also has a circular shoulder 46 extending into the passage 40, which acts as a set for a sintered metal plug 48.

The sintered metal plug 48 provides a calibrated leak path through the passage 40. The sintered metal plug 48 can be formed from stainless steel, brass, or other suitable materials. The sintered plug 48 is porous and defines a plurality of flow passages through it to permit an adequate amount of refrigerant to flow through the plug 48 for reliable detection, yet limit the amount of refrigerant that will be released to the environment. A sintered metal plug sized for a 600 cm$^3$/min flow rate when exposed to a source of 100 psig of nitrogen gas and vented to one atmosphere is suitable. Sintered plugs with flow rates within a tolerance of fifteen percent of 600 cm$^3$/min are presently preferred. The sintered plug 48 can be installed into the passage 40 of the body 30 using a guided hand-operated press. However, the sintered plug 48 tends to compress when so installed, decreasing its porosity, and exhibiting a lower rate of through flow. Therefore, an uninstalled sintered plug with a flow through rate greater than 600 cm$^3$/min is used to form the sensing unit 14. It has been found that uninstalled sintered plugs with flow rates of about 750 cm$^3$/min are suitable. Sintered plugs are commercially available from Mott Corporation of Farmington, Conn. Such plugs, when installed and compressed, provide the desired flow rate of about 600 cm$^3$/min. This flow rate specification will provide adequate refrigerant flow from a 60 to 200 psig source for detection in the 100 cm$^3$/min to 1000 cm$^3$/min range to deliver adequate leak sealant additive to initiate a sealing reaction within or on the sintered plug and limit refrigerant loss to less than five percent, and preferably less than three percent, of the total refrigerant charge of a typical automotive air conditioning system during a three minute testing period. Thus, the sintered plug 48 provides both a flow-restricting passage through its internal passageways, and also a seal-forming surface on which any leak sealant additive that may be present can form a sealant plug to fully or partially occlude the passage 40. As used herein, the term "seal-forming surface" means any surface on which a leak sealant additive can consistently begin forming a sealant plug to at least partially reduce refrigerant flow rate through the sensing unit. Such a surface is adjacent to the flow path and has a large enough surface area to allow the sealant plug to begin forming before five percent of the refrigerant charge within the air conditioning system has been vented.

In order to minimize the chance of unintended clogging, it is recommended that the sensing unit 14 be provided in a sealed bag or that both the inlet 42 and outlet 44 be provided with removable seals. The sensing unit 14 should remain sealed until immediately prior to use. In use, refrigerant gas will enter the passage 40 through inlet 42, travel through passage 40, and come to sintered plug 48. The circular shoulder 46 of the body 30 prevents pressure of entering refrigerant from dislodging the sintered plug 48. Refrigerant then passes through sintered plug 48, continues through passage 40, and exhausts through outlet 44. In the presence of moisture, and in some cases the presence of oxygen, refrigerant that contains a leak sealant additive will begin to form a seal on or within the flow passages in sintered plug 48, thereby reducing the total flow rate of refrigerant through sensing unit 14.

Figure 4:
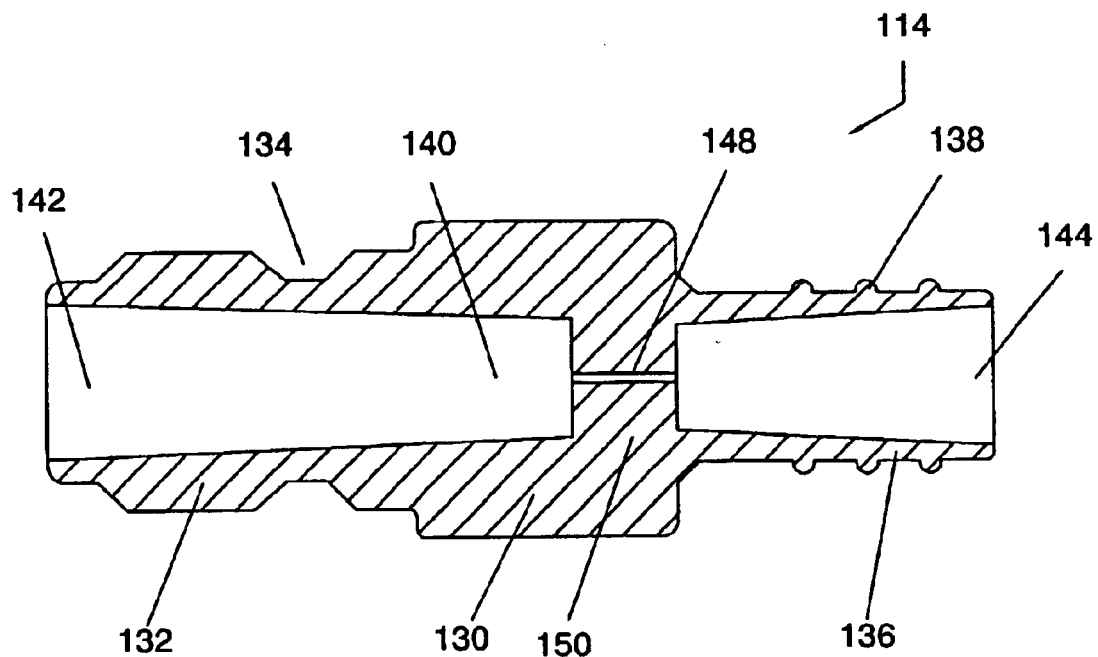
FIG. 4 is cross-sectional view of a second embodiment of a sensing unit according to the present invention.

FIG. 4 shows a second embodiment of a sensing unit 114. Sensing unit 114 has a tubular body 130 that uses a core 150 with a machined orifice 148 as the calibrated leak path in passage 140. In the sensing unit 114, the seal-forming surface is the interior surface of the core 150 adjacent to the machined orifice 148. The machined orifice 148 is sized to provide enough refrigerant flow for ease of flow detection, yet limit the amount of refrigerant that will be vented to the environment. The machined orifice 148 is sized in the 50 to 100 micron (0.002 to 0.004 inch) diameter range. This diameter specification will provide adequate refrigerant flow from a 60 to 200 psig source for detection in the 100 cm$^3$/min to 1000 cm$^3$/min range, deliver adequate leak sealant additive to initiate seal formation on the core 150 or within the orifice 148, and limit refrigerant loss to a maximum of five percent, and preferably three percent, of the total refrigerant charge of a typical automotive air conditioning system during a time period of three minutes. The sensing unit 114 includes additional features that are similar to the analogous elements of the sensing unit 14 of FIG. 3. These features include an inlet 142 at a quick-disconnect end 132 with recess 134, and an outlet 144 at an open tube stub end 136 having ribs 138.

In use, refrigerant gas enters the sensing unit 114 through inlet 142, travels through passageway 140 and comes to the core 150 with machined orifice 148. Refrigerant then passes through the machined orifice 148, and exhausts through the outlet 144. In the presence of moisture, and in some cases the presence of oxygen, refrigerant that contains a leak sealant additive will begin to form a seal on the core 150 at the inlet of or within the machined orifice 148, thereby reducing the total flow rate of refrigerant through sensing unit 114.

The use of the sintered metal plug 48 in place of the core 150 with the orifice 148 is preferred. The sintered metal plug 48 provides multiple small diameter leak paths that are more easily sealed by the leak sealant additive compared to a larger single orifice hole. Additionally, the sintered metal plug 48 is less prone to clogging by materials other than leak sealant additives such as moisture desiccants, particulate matter, refrigerant oils, leak tracer dyes, etc. Therefore, if a single orifice sensing unit, such as sensing unit 114, is used, it is recommended that a filtering device upstream of the sensing unit 114 be employed to prevent accidental clogging. Alternatively, sensing unit 114 can be outfitted with a screen, between the inlet 142 and the core 150. The screen could be filter paper, mesh or sintered metal of an appropriate configuration to filter particulate, while not affecting the flow through rate of the sensing unit 114. For example, if sintered metal is used as the screen, it should have a rating of about 50 to 100 microns, thereby preventing particulate from clogging the orifice 148, while not affecting the rate of refrigerant flow through the sensing unit 114 if a leak sealant additive begins to form a sealant plug on the screen. The flow rate through the sensing unit 114 is instead governed by the calibrated orifice 148 and any sealant plug formed on its adjacent seal-forming surface.

The method of the present invention will now be described with reference to FIG. 5, which shows a test rig 210 fitted with a sensing unit 14 and connected to a typical R12-based air conditioning system or refrigerant store service port 302. Similar operation is achieved using test rig 10 for R134a based air conditioning systems or test rig 110 fitted with sensing unit 114, the differences in the seal-forming surfaces and refrigerant flow-restricting passages between the two embodiments having already been described. Before connecting test rig 210 to the service port 302, sensing unit 14 is wetted on the inside of both openings. As used herein, wetting is meant to include any method of introducing moisture to at least one inside surface of a sensing unit, preferably between the flow-restricting passage and the inlet, such as by directly pouring or injecting ordinary tap water into an open end of the sensing unit 14, immersing the entire sensing unit in water, or introducing a moist article. Excess water can then be removed from the interior of the sensing unit 14 by shaking it several times to leave a trace of moisture droplets 300. The introduction of moisture into the sensing unit provides an accelerator for seal formation during testing should a leak sealant additive be present in the test refrigerant.

After wetting, the sensing unit 14 is connected to quick-disconnect fitting 222 of test rig 210. Quick-disconnect fitting 222, like its analogous elements in the first two embodiments, is commercially available. The fitting 222 includes a body 260, sealing o-ring 262, retaining balls 264, and coupler actuator 266. A transfer tube, such as transfer tube 16 of FIG. 1, can connect the tube stub 36 to a flow indicator. The test rig 210 is then connected to the air conditioning system or refrigerant store service port 302, which has an access valve 304. A high-side service coupler 220 of the test rig 210 has an elastomeric seal 270 capable of withstanding exposure to refrigerant, a valve depressor 272, containment cup 274, tube 276, body 278, and connection nut 280. Valve depressor 272 depresses service port valve 304 while seal 270 seals port 302, preventing refrigerant from escaping to the environment at the connection.

Once valve 304 is actuated, refrigerant flow will travel in the direction of arrow A through coupler 212 (through service coupler 220 and quick-disconnect fitting 222), through sensing unit 14, through a transfer tube and through a flow indicator (such as those shown in FIGS. 1 and 2) where an indication of initial refrigerant flow will be displayed. If the refrigerant contains no leak sealant additive, the flow meter will indicate a constant flow rate throughout the duration of the test. If the refrigerant contains a leak sealant additive, the additive will combine with the water droplets 300, and in some cases the ambient oxygen, to begin to form a sealant plug on the seal-forming surface of the sensing unit 14 (on or in the sintered metal plug 48). If a sealant plug forms, the flow indicator will indicate a flow reduction or a complete loss of flow during the test period. It is expected that a three-minute test period is more than adequate to detect a reduction of flow rate in the presence of a leak sealant additive. Over a three-minute period, an observed reduction of from 40 to 100 percent of the original initial flow rate can be expected if leak sealant additive is present in the refrigerant.

Once the flow has been established as constant, diminishing or absent, the test rig 210 is removed from the air conditioning refrigerant access port 302. The limited time period of testing, together with the limited flow rate through the sensing unit 14, limits the amount of refrigerant charge vented to the atmosphere.

After testing has been completed, sensing unit 14 can be removed from coupler 212 and the transfer tube and discarded. A new sensing unit 14 can be installed onto coupler 212 and to the transfer tube to prepare the test rig 210 for another test.

Figure 5:
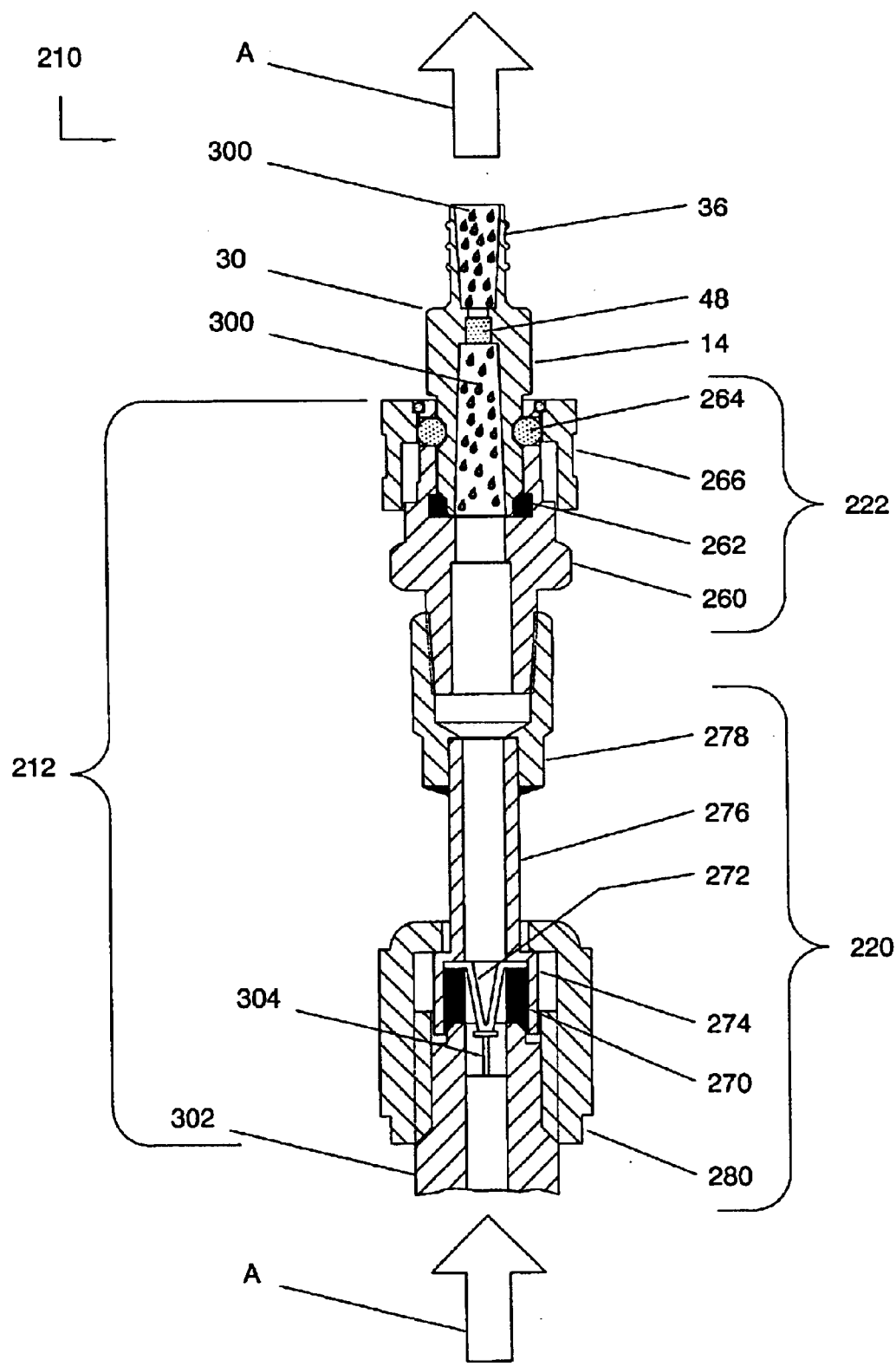
FIG. 5 is a cross-sectional view of a test rig in use while fitted with the sensing unit of FIG. 3.

It should be again noted that the test rig 210 depicted in FIG. 5 would find use primarily in automotive R12 refrigerant-based air conditioning systems. Modification of service coupler 212 can enable test rig 210 to be connected on other air conditioning systems that contain other refrigerant types, for example R134a, R22, R500 and R502. FIG. 1 is an example of a R134a test rig that would be used on R134a based air conditioning systems.

What is claimed is:

1. A device for detecting the presence of a leak sealant additive in a refrigerant charge, the device comprising:
a sensing unit comprising a flow-restricting passage calibrated to allow a preselected rate of refrigerant flow therethrough, a seal-forming surface comprising a porous insert adjacent the passage, an inlet in fluid communication between the passage and a refrigerant charge, and an exhaust outlet opposite the inlet.

2. The device of claim 1 further comprising a coupler having a first end adapted to engage and open a refrigerant access port in an air conditioning system, and a second end adapted to mate with the inlet of the sensing unit.

3. The device of claim 2 further comprising a flow indicator with an inlet in fluid communication with the exhaust outlet of the sensing unit.

4. The device of claim 3 further comprising a transfer tube for establishing fluid communication between the exhaust outlet and the flow indicator.

5. The device of claim 1 wherein the porous insert comprises sintered metal.

* * * * *